United States Patent
Devereux et al.

(10) Patent No.: US 8,163,785 B2
(45) Date of Patent: *Apr. 24, 2012

(54) PYRAZOLO[5,1B]OXAZOLE DERIVATIVES AS CRF-$_1$ RECEPTOR ANTAGONISTS

(75) Inventors: Nicholas James Devereux, Ash (GB); Jeffrey McKenna, Horsham (GB)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/017,243

(22) Filed: Jan. 31, 2011

(65) Prior Publication Data

US 2011/0190360 A1    Aug. 4, 2011

Related U.S. Application Data

(60) Provisional application No. 61/300,231, filed on Feb. 1, 2010.

(51) Int. Cl.
 *A61K 31/424* (2006.01)
 *C07D 498/14* (2006.01)
(52) U.S. Cl. ........................ 514/375; 548/218
(58) Field of Classification Search .................. 514/375; 548/218
See application file for complete search history.

(56) References Cited

U.S. PATENT DOCUMENTS

2002/0183375 A1    12/2002 Dubowchik et al.

OTHER PUBLICATIONS

Meena V. Patel et al., "Synthesis of 4,5-Diaryl-1$H$-pyrazole-3-ol Derivatives as Potential COX-2 inhibitors" *J. Org. Chem.* 69:7058-7065, 2004.
John E. Tellew et al., "Small Molecule Antagonists of the Corticotropin Releasing Factor (CRF) Receptor: Recent Medicinal Chemistry Developments" *Current Topics in Medicinal Chemistry* 8:506-520, 2008.

*Primary Examiner* — Rebecca Anderson
*Assistant Examiner* — Samantha Shterengarts
(74) *Attorney, Agent, or Firm* — Michael G. Smith

(57) ABSTRACT

There are described 4-difluoromethoxyphenyl pyrazolo[5.1-b]oxazole derivatives of Formula I:

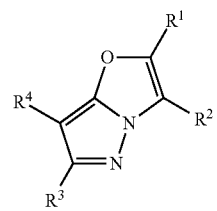

which are useful as corticotropin releasing factor (CRF) receptor antagonists and as pharmaceuticals.

11 Claims, No Drawings

PYRAZOLO[5,1B]OXAZOLE DERIVATIVES AS CRF-1 RECEPTOR ANTAGONISTS

CROSS-REFERENCE TO RELATED APPLICATION

This application claims the benefit of U.S. Provisional Application No. 61/300,231 filed Feb. 1, 2010, which is incorporated herein by reference.

FIELD OF THE INVENTION

The present invention relates to 4-difluoromethoxyphenyl pyrazolo[5.1-b]oxazole derivatives their preparation, their use as pharmaceuticals and pharmaceutical compositions containing them. More particularly the present invention relates to their use as corticotropin releasing factor ($CRF_1$) receptor antagonists.

SUMMARY OF THE INVENTION

In a first aspect of the invention we provide a compound of formula I;

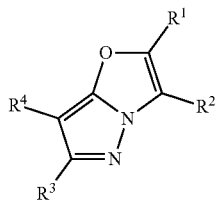

I in which $R^1$ and $R^3$, which may be the same or different, are each hydrogen, alkyl C1 to 6 or halo alkyl C1 to 6;

$R^2$ is difluoromethoxyphenyl, in which the phenyl may be optionally substituted by one or more of alkyl C1 to 6, alkoxy C1 to 6, halo, haloalkyl C1 to 6, thioalkyl C1 to 6, —$NR^5R^6$, —CN, haloalkoxy C1 to 6, aryl or -Het or two adjacent carbons are substituted by —$O(CH_2)_xO(CH_2)_y$—;

Het is a 5- or 6-membered heteroaryl or a 4, 5- or 6-membered heterocycle;

$R^4$ is alkylene C2 to 10, hydroxy alkyl C1 to 10, each of which may optionally be substituted by aryl, or is —$OR^7$, —$(CH_2)_mNR^8R^9$, —$COR^{10}$, a 5- or 6-membered heteroaryl or a 5- or 6-membered heterocycle, the 5- or 6-membered heteroaryl or 5- or 6-membered heterocycle being optionally substituted by one or more substituents selected from the group alkyl C1 to 10, haloalkyl C1 to 10, hydroxyalkyl C1 to 10, alkoxy(C1 to 3)alkyl(C1 to 3), halo, —$CO_2R^{19}$, —$CONR^{20}R^{21}$, aryl or a 5- or 6-membered heterocycle or heteroaryl;

$R^5$ and $R^6$, which may be the same or different, are each hydrogen or alkyl C1 to 6 or $R^5$ and $R^6$, together with the nitrogen to which they are attached, form an optionally substituted saturated or unsaturated cyclic group;

$R^7$ is alkyl C1 to 10, cycloalkyl C3 to 10, optionally fused to an aryl, alkyl(C1 to 6)-cycloalkyl(C3 to 6)-, hydroxy alkyl C1 to 10, hydroxyalkyl(C1 to 6)-(haloalkyl C1 to 6), alkyl(C1 to 6)-oxy-alkyl(C1 to 6), —$(CH_2)_qCOOR^{22}$ or a 5- or 6-membered heterocycle; each of which is optionally substituted by one or more of alkyl C1 to 10, alkoxy C1 to 10, hydroxyalkyl C1 to 10, aryl or a 5- or 6-membered heteroaryl, the aryl or a 5- or 6-membered heteroaryl being optionally substituted by alkyl C1 to 10;

$R^8$ and $R^9$, which may be the same or different, are each hydrogen, alkyl C1 to 10, halo alkyl C1 to 10, alkyl(C1 to 6)-oxy-alkyl(C1 to 6), —$COOR^{11}$, —$COR^{12}$ or arylalkyl C1 to 6 or together with the nitrogen to which they are attached $R^8$ and $R^9$ form a 5- or 6-membered heterocycle, optionally substituted by one or more of alkyl C1 to 6;

m is an integer 0 or 1;
q is an integer from 1 to 6;
x and y, which may be the same or different, are each an integer from 1 to 6;
$R^{10}$ is hydrogen, alkyl C1 to 6, —$NR^{13}R^{14}$, hydroxy or alkoxy C1 to 6;
$R^{12}$ is alkyl C1 to 10, aryl or is a 5- or 6-membered unsaturated heterocyclic ring;
$R^{13}$ and $R^{14}$, which may be the same or different, are each alkyl C1 to 10, cycloalkyl C3 to 10, cycloalkyl(C3 to 6)alkyl (C1 to 6)-, alkoxy C1 to 10, haloalkyl C1 to 10, aryl, a 5- or 6-membered heterocycle or heteroaryl comprising 1, 2 or 3 heteroatoms; each of which may be optionally substituted by aryl or heteroaryl, or $R^{13}$ and $R^{14}$ together with the nitrogen to which they are attached form a 5- or 6-membered heterocycle comprising 1, 2 or 3 heteroatoms, which may optionally be fused to a phenyl group, said heterocycle and optionally fused phenyl group being optionally substituted by one or more of alkoxy C1 to 10;
$R^{22}$ is hydrogen or alkyl C1 to 6;
$R^{11}$ is alkyl C1 to 6 or aryl;
$R^{19}$ is hydrogen or alkyl C1 to 10;
$R^{20}$ and $R^{21}$, which may be the same or different, are each alkyl C1 to 10; and isomers thereof,
in free form or as a pharmaceutically acceptable salt.

For purposes of interpreting this specification, the following definitions will apply and whenever appropriate, terms used in the singular will also include the plural and vice versa.

As used herein, the term "alkyl" refers to a fully saturated, branched or unbranched hydrocarbon moiety, i.e. primary, secondary or tertiary alkyl or, where appropriate, cycloalkyl or alkyl substituted by cycloalkyl, they may also be saturated or unsaturated alkyl groups. Where not otherwise identified, preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Preferably, the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-7, more preferably about 1-4 carbons.

As used herein, the term "heterocyclic" or "heterocyclo" refers to an optionally substituted, saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

The term substituted heterocycle further refers to heterocyclic groups as defined herein substituted with 1, 2 or 3 substituents selected from the groups consisting of the following:
(a) alkyl;
(b) hydroxy (or protected hydroxy);
(c) halo;
(d) haloalkyl;
(e) oxo, i.e., =O;
(f) amino, alkylamino or dialkylamino;
(g) alkoxy;
(h) cycloalkyl;
(i) carboxyl;
(j) heterocyclooxy, wherein heterocyclooxy denotes a heterocyclic group bonded through an oxygen bridge;
(k) alkyl-O—C(O)—;
(l) mercapto;
(m) nitro;
(n) cyano;
(o) sulfamoyl or sulfonamido;
(p) aryl;
(q) alkyl-C(O)—O—;
(r) aryl-C(O)—O—;
(s) aryl-S—;
(t) aryloxy;
(u) alkyl-S—;
(v) formyl, i.e., HC(O)—;
(w) carbamoyl;
(y) aryl-alkyl-; and
(z) aryl substituted with alkyl, cycloalkyl, alkoxy, hydroxy, amino, alkyl-C(O)—NH—, alkylamino, dialkylamino or halogen.

As used herein, the term "aryl" refers to an aromatic carbocyclic ring system containing 6 to 14 ring carbon atoms, which may be unsubstituted or substituted as defined.

As used herein, the term "aryloxy" refers to both an —O-aryl and an —O-heteroaryl group, wherein aryl and heteroaryl are defined herein.

As used herein, the term "heteroaryl" refers to a 5-14 membered monocyclic- or bicyclic- or polycyclic-aromatic ring system, having 1 to 8 heteroatoms selected from N, O or S. Preferably, the heteroaryl is a 5-10 or 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinolinyl, 1-, 3-, 4-, 5-, 6-, 7-, or 8-isoquinolinyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenanthrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoquinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

A heteroaryl group may be mono-, bi-, tri-, or polycyclic, preferably mono-, bi-, or tricyclic, more preferably mono- or bicyclic.

As used herein, the term "halogen" or "halo" refers to fluoro, chloro, bromo, and iodo.

Halo alkyl shall include mono- and poly-halogenated alkyl, e.g. mono-, di- or tri-substituted. When more than one halo atom is present they may be the same or different.

$R^1$ and $R^3$ are each preferably methyl.

$R^2$ is preferably a 4-difluoromethoxyphenyl, in which the phenyl is substituted as hereinbefore described. $R^2$ is more preferably 4-difluoromethoxy-2-methylphenyl:

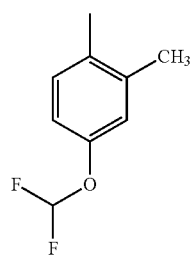

$R^4$ is preferably alkyl(C1 to 6)-oxy-alkyl(C1 to 6), heteroaryl, —$(CH_2)_m NR^8 R^9$ or —$COR^{10}$. Thus, $R^4$ is preferably an amide, e.g. a —CON-amide or a —NCO— amide, an ether or a heteroaryl. When $R^4$ is a heteroaryl it may be a pyrazole, an imidazole or a triazole, each of which may be optionally substituted as hereinbefore described. In one aspect of the invention $R^4$ is an optionally substituted pyrazole. In another aspect of the invention $R^4$ is an optionally substituted triazole. $R^4$ is most preferably 3,5-dimethyl-1H-1,2,4-triazol-1-yl:

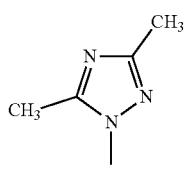

When $R^5$ and $R^6$ together form an optionally substituted saturated or unsaturated cyclic group it may be a 5- or 6-membered ring. When $R^5$ and $R^6$ together form an optionally substituted saturated cyclic group, the cyclic group may be piperidine, morpholine, piperazine or azetidine.

Specific compounds of formula I which may be mentioned include:
  3-(4-(difluoromethoxy)-2-methylphenyl)-7-(3,5-dimethyl-1H-1,2,4-triazol-1-yl)-2,6-dimethylpyrazolo[5,1-b]oxazole;
  and isomers thereof,
  in free form or as a pharmaceutically acceptable salt.

Another aspect of this invention relates to the fact that the compounds of formula I and their pharmaceutically acceptable salts have beneficial pharmacological activity and, therefore, are useful as pharmaceuticals.

Therefore, according to a further aspect of the invention we provide a compound of formula I as hereinbefore described as a medicament. More particularly, we provide a compound of formula I as hereinbefore described as a corticotropin releasing factor ($CRF_1$) receptor antagonist.

According to a further aspect of the invention we provide the use of a compound of formula I as hereinbefore described in the manufacture of a medicament. More particularly, we provide the use as hereinbefore described in the manufacture of a medicament for a corticotropin releasing factor ($CRF_1$) receptor antagonist.

Furthermore it has now been found that the compounds of formula I, or a salt thereof, behave as CRF, receptor antagonists.

The CRF-1 or CRF-2a receptor activity of the agents of the invention has been determined in vitro in the following way:

Chinese hamster ovary (CHO) cells expressing either the human recombinant CRF-1 or CRF-2a receptors (Chen et al., Proc Natl Acad Sci USA 90, 8967-8971, 1993; Liaw et al., Endocrinology 137, 72-77, 1996) are propagated in Dulbecco's modified Eagle medium supplemented with 10% foetal calf serum, non-essential amino acids, 100 U/ml penicillin, 100 mg/l streptomycin and 1 g/l geneticin (G418). For cyclic AMP determinations the Homogeneous Time-Resolved Fluoresce (HTRF) cAMP dynamic 2 kit (Cishbio International, France) was used as per manufacturers' instructions. CHO cells, previously cryopreserved, were thawed, centrifuged for 7 mins at 1200 rpm and resuspended in serum free media, then pipetted out onto clear bottomed black tissue culture treated 384-well microtitre plates (Corning Inc, US) at 2,000 cells per well. Compounds of the invention, prepared in DMSO, and subsequently diluted 50 fold in assay buffer (1× Hanks balanced salt solution, 0.2% (w/v) bovine serum albumin, 1.7 mM isobutylmethylxanthine and 10 mM Hepes, pH7.4) are then added onto the cell containing plate where a further 2 fold dilution is performed and incubated for 15 min. Following incubation, buffer containing a 5 times final concentration of agonist is added to the plate and incubated for 30 min. Finally, d2 dye labelled cAMP and cryptate labelled anti-cAMP antibody, both made in lysis buffer, are added to the plate followed by a settling period of 1 hour. During the settling period cAMP produced by the cells competes with the d2 labelled cAMP for the anti-cAMP cryptate. The plate is read on the Pherastar (BMG, Germany). Increasing levels of endogenous cAMP produced by cells can be followed by a decrease of fluorescent signal and vice versa. Values represented by a change in arbitrary fluorescence units are converted into cAMP concentrations by use of a standard curve the reagents for which are supplied with the kit. Antagonist dose response curves (1 nM-30 μM) are constructed in the presence of 1 nM CRF. IC50 values of antagonists are calculated by fitting the percent inhibition of the effect of CRF by increasing concentrations of the antagonists. The fit is performed using the nonlinear logistic function of the Activity-base software package v 5.4.5.27 (IDBS, UK).

In this test, the agents of the invention show CRF, antagonistic activity with IC50 CRF, values of about 1 nM to 30 μM, preferably 1 nM to 10 μM.

Compounds of the invention are useful in the treatment of any state with increased endogenous level of CRF (corticotropin releasing factor) or in which the HPA (hypothalamic pituitary axis) is disregulated, or of various diseases induced or facilitated by CRF.

Compounds of the invention are in particular useful in the treatment or prevention of gastrointestinal disorders including irritable bowel syndrome with or without diarrhoea, inflammatory bowel diseases, post-operative ileus, reflux disease and infectious diarrhoea.

Compounds of the invention are also in particular useful in the treatment or prevention of major depressive disorders including bipolar depression, unipolar depression, single or recurrent major depressive episodes with or without psychotic features, catatonic features, melancholic features, atypical features or postpartum onset, the treatment of anxiety and the treatment of panic disorders. Other mood disorders encompassed within the term major depressive disorders include fatigue syndrome and dysthymic disorder with early or late onset and with or without atypical features, neurotic depression, post traumatic stress disorders, post operative stress and social phobia; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

Compounds of the invention are also useful in the treatment or prevention of schizophrenic disorders including paranoid schizophrenia, disorganised schizophrenia, catatonic schizophrenia, undifferentiated schizophrenia, residual schizophrenia.

Compounds of the invention are also useful in the treatment or prevention of neurodegenerative diseases such as Alzheimer's disease, Parkinson's disease, Huntington's disease, senile dementia of the Alzheimer's type, and multiinfarct dementia.

Compounds of the invention are useful as analgesics. In particular they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; burns; scar pain; itch; and thalamic pain such as post stroke thalamic pain.

Compounds of the invention are also useful for the treatment of dysfunction of appetite and food intake and in circumstances such as anorexia, anorexia nervosa, bulimia, obesity and metabolic syndrome.

Compounds of the invention are also useful in the treatment of sleep disorders including dysomnia, insomnia, sleep apnoea, narcolepsy, and circadian rhythmic disorders.

Compounds of the invention are also useful in the treatment or prevention of cognitive disorders. Cognitive disorders include dementia, amnestic disorders and cognitive disorders not otherwise specified.

Furthermore compounds of the invention are also useful as memory and/or cognition enhancers in healthy humans with no cognitive and/or memory deficit.

Compounds of the invention are also useful in the treatment of tolerance to and dependence on a number of substances. For example, they are useful in the treatment of dependence on nicotine, alcohol, caffeine, phencyclidine (phencyclidine like compounds), or in the treatment of tolerance to and dependence on opiates (e.g. cannabis, heroin, morphine) or benzodiazepines; in the treatment of cocaine, sedative ipnotic, amphetamine or amphetamine-related drugs (e.g. dextroamphetamine, methylamphetamine) addiction or a combination thereof.

Compounds of the invention are also useful as anti-inflammatory agents. In particular they are useful in the treatment of inflammation in asthma, influenza, chronic bronchitis and rheumatoid arthritis; in the treatment of inflammatory diseases of the gastrointestinal tract such as Crohn's disease, ulcerative colitis, postoperative gastric ileus (POI), inflammatory bowel disease (IBD) and non-steroidal anti-inflammatory drug induced damage; inflammatory diseases of the skin such as herpes and eczema; inflammatory diseases of the bladder such as cystitis and urge incontinence; and eye and dental inflammation.

Compounds of the invention are also useful the treatment of fertility problems, sexual dysfunctions and pre-term birth and non-inflammatory urogenital disorders such as overactive bladder and related urinary incontinence.

Compounds of the invention are also useful in the treatment of allergic disorders, in particular allergic disorders of the skin such as urticaria, and allergic disorders of the airways such as rhinitis.

Compounds of the invention are also useful the treatment of mast cell activation disorders such as mastocytosis.

Compounds of the invention are also useful the treatment of Cushing's syndrome induced by drugs such as steroids or cancer such as pituitary adenoma.

Compounds of the invention are also useful in the treatment of emesis, i.e. nausea, retching and vomiting. Emesis includes acute emesis, delayed emesis and anticipatory emesis. The compounds of the invention are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease, acid indigestion, over-indulgence of food or drink, acid stomach, sour stomach, regurgitation, heartburn, such as episodic heartburn, nocturnal heartburn, and meal-induced heartburn and dyspepsia.

Compounds of the invention are of particular use in the treatment of gastrointestinal disorders such as irritable bowel syndrome; skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

Compounds of the invention are useful for the treatment of neurotoxic injury which follows cerebral stroke, thromboembolic stroke, hemorrhagic stroke, cerebral ischemia, cerebral vasospam, hypoglycemia, hypoxia, anoxia, perinatal asphyxia cardiac arrest.

The utility of the agents of the invention in the above indicated diseases could be confirmed in a range of standard tests. (1) The anxiolytic activity of the agents of the invention can be confirmed in the mouse elevated plus-maze [see for example Rodgers R. J., Behavioural Pharmacology 8: 477-496 (1997) where the relevance of the elevated plus-maze is discussed on p. 486; for the method, see Rodgers R. J. et al. Ethology and Psychopharmacology (Eds S J Cooper and C A Hendrie), pp 9-44 (1994), J. Wiley, Chichester]. (2) The analgesic activity of the agents of the invention can be confirmed in rat visceral hyperalgesia models following colorectal distension [see for example Schwetz I, Am J Physiology 286: G683-G691 (2004); for the method, see Ness T. J., Brain Research 450:153-169 (1988)]. (3) The anti-diarrheal activity of the agents of the invention can be confirmed in rat defecation models during stress or CRF challenge [see for example Maillot C., Gastroenterology 119:1569-1579 (2002)].

In these tests, the agents of the invention show anxiolytic-like, visceral analgesic and anti-diarrheal effects following oral administration of 0.1 to 30 mg/kg.

For the above-mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 100 mg/kg, preferably from about 1 to about 30 mg/kg animal body weight. In larger mammals, for example humans, an indicated daily dosage is in the range from about 1 to about 500 mg, preferably from about 1 to about 100 mg of an agent of the invention, conveniently administered, for example, in divided doses up to three times a day or in sustained release form.

The agents of the invention may be administered by any conventional route, in particular enterally, preferably orally, for example in the form of tablets or capsules, or parenterally, for example in the form of injectable solutions or suspensions.

In accordance with the foregoing, the present invention also provides an agent of the invention, for use as a pharmaceutical, e.g. for the treatment of diseases induced or facilitated by CRF, such as these indicated above.

Therefore, according to a further aspect of the invention we provide a compound of formula I, or a salt thereof, for the treatment or alleviation of treatment of any state with increased endogenous level of CRF or in which the HPA (hypothalamic pituitary axis) is disregulated, or of various diseases induced or facilitated by CRF.

The agents of the invention can be administered in vivo either alone or in combination with other pharmaceutical agents, e.g. agents effective in the treatment of diseases and conditions in which an increased endogenous level of CRF plays a role or is implicated. A suitable combination consists of a compound of the present invention with one or more compounds selected from the group consisting of dopamine D2 receptor antagonists, serotonin 5-HT4 receptor agonists, serotonin 5-HT3 receptor agonists, serotonin 5-HT3 receptor antagonists, CCK1 receptor antagonists, motilin receptor agonists, μ-opioid receptor antagonists, opioid receptor agonists and opiates, other CRF-1 receptor antagonists, glutamate receptor antagonists, neurokinin receptor antagonists, histamine H2 receptor antagonists, histamine H4 receptor antagonists, proton pump inhibitors, chloride channel activators, guanylate cyclase-c activators, muscarinic receptor antagonists, antispasmodics, stimulant laxatives, osmotic laxatives, faecal softeners, absorbents and fibre supplements, antacids, GI relaxants, bismuth compounds, vanilloid receptor antagonists, anticonvulsants, NSAIDS, COX-2 inhibitors, GABAb receptor modulators, CB receptor ligands, calcium channel blockers, sodium channel blockers, tricyclic antidepressants, serotonin and noradrenaline re-uptake inhibitors, benzodiazepines, alpha-2 receptor agonists and ghrelin receptor agonists.

More specifically, a compound of the present invention may be administered as a combination with one or more compounds selected from the group consisting of dopamine D2 receptor antagonists, such as, chlorpromazine, prochlorperazine, haloperidol, alizapride, domperidone, metoclopramide and itopride; serotonin 5-HT4 receptor agonists, such as, cisapride, cinitapride, mosapride, renzapride, prucalopride, tegaserod, velusetrag, ATI-7505 and compounds described in WO 2005068461, US 2005228014, WO 2005080389, US 2006100426, US 2006100236, US 2006135764, US 2005277671, WO 2005092882, WO 2005073222, JP 2005104896, JP 2005082508, WO 2005021539, JP 2004277319, JP 2004277318, WO 2004026869, EP 1362857, WO 2006108127, US 20060183901, WO 2006127815, US 20060276482, WO 2007005951, WO 2007010390, WO 2007005951, WO 2007048643, WO 2007096352, WO 2007068739 and WO 20070117796; serotonin 5-HT3 receptor agonists, such as, pumesotrag and compounds described in WO 2007004041; serotonin 5-HT3 receptor antagonists, such as, alosetron, cilansetron, ramosetron, azasetron, ondansetron, granisetron, tropisetron, DDP225 and compounds described in WO 2006183769, WO 2006105117 and WO 2007004041; CCK1 receptor antagonists, such as, JNJ-17156516, devazepide, loxiglumide and dexloxiglumide; motilin receptor agonists, such as, motilin, atilmotin, erythromycin, alemcinal, mitemcinal, KOS-2187, 1-[4-(3-fluoro-phenylamino)-piperidin-1-yl]-2-[4(S)-3-methyl-piperazin-1-ylmethyl)-phenyl]-ethanone and compounds described in WO 2005060693, WO 2006127252, WO 2007007018, WO 2007012479 and WO 2008000729; m-opioid receptor antagonists, such as, naloxone, alvimopan, methylnaltrexone and compounds described in US 20050203123, US 2006063792, WO 2007050802, US 2007103187, WO 2009029252, WO 2009029256, WO 2009029257 and WO 2009029253; opioid receptor agonists and opiates, such as, morphine, buprenorphine, diamorphine, dihydrocodeine, fentanyl, pethidine, asimadoline, loperamide and codeine; CRF-1 receptor antagonists, such as, GSK876008, pexacerfont and compounds described in WO 2004069257, WO 9940089, US 6844351, WO 2005013997, WO 2005014557, WO 2005023806, WO 2005026126, WO 2005028480, WO 005044793, WO 2005051954, WO 2005051954, WO 2005115399, WO 2005028480, WO 2005023806, WO 2006044958, WO 2006044821 and US 20060211710; glutamate receptor antagonists, such as, AZD9272, AZD2066, AFQ056, ADX-48621 and compounds described in WO 9902497, WO 2000020001, WO 200304758 and WO 2005030723, WO 2005077345, US 2006009443, EP 1716152, WO 2005080397, US 2006019997, WO 2005066155, WO 2005082884, WO 2005044266, WO 2005077373, EP 1713791, EP 1720860, WO 2005080379, EP 1716130, US 2006235024, WO 2005080363 WO 2006114264, WO 2006114260, WO 2006089700, WO 2006114262, WO 2006123257, US 2005272779, WO 2006048771, WO 2006123249, US 2006009477, WO 2006014185, EP 1723144, US 2006025414, US 2006004021, US 2006160857, WO 2006074884, WO 2006129199, WO 2006123244, WO 2006123255, WO 2007040982, WO 2007023290, WO 2007023242, WO 2007050050, WO 2007039781, WO 2007039782 and WO 2007023245; neurokinin receptor antagonists, such as, taletant, osanetant, casopitant, nepadutrent, saredutant, DNK-333, SLV-317, SLV321, SLV317 and compounds described in EP 96-810237, WO 2006137790, WO 2006137791, WO 2006094934, WO 2007037742 and WO 2007037743; histamine H2 receptor antagonists, such as, famotidine, cimetidine, ranitidine and nizatidine; histamine H4 receptor antagonists, such as, JNJ7777120, JNJ10191584 and compounds described in US 2006111416, WO 2006050965, WO 2005092066, WO 2005054239 US 2005070550, US 2005070527, EP 1505064, WO 2007090852, WO 2007090853, WO 2007090854, US 20070232616, US 20070238771, WO 2007117399, WO 2007031529 and WO 2007072163; proton pump inhibitors, such as, omeprazole, lansoprazole, rabeprazole, tentoprazole, pantoprazole, esomeprazole, revaprazan, soraprazan and AGN201904; chloride channel activators, such as, lubiprostone; guanylate cyclase-2c activators, such as, linaclotide, guanilib, guanylin, uroguanylin and compounds described in WO 2005087797, WO 2005016244, WO 2007022531, WO 2007101158, WO 2007101161 and US 7041786; muscarinic receptor antagonists, such as, darifenacin, solifenacin, atropine, dicycloverine, hycosine butyl bromide, propantheline, oxybutinin, cimetropium bromide and pinaverium bromide; antispasmodics, such as, mebeverine, octylonium bromide, trimebutine, tiropramide, alverine and peppermint oil; stimulant laxatives, such as, bisacodyl; osmotic laxatives, such as, activated charcoal with sorbitol, lactulose, magnesium hydroxide and phosphate buffered saline; faecal softeners, such as, senna concentrate, liquid paraffin and arachis oil; absorbents and fibre supplements; bulk fibre laxatives such as bran, methylcellulose, ispaghula husk and sterculia; antacids, such as, aluminium, magnesium and calcium antacids, simeticone and alginate containing preparations; GI relaxants, such as, cholestyramine resin; bismuth compounds, such as, bismuth subsalicylate; vanilloid receptor antagonists, such as, SB-705498, ABT-102, AZD1386, GRC-6211, MK-2295 and compounds described in WO 2002076946, WO 2004033435, WO 2005121116, WO 2005120510, WO 2006006740, WO 2006006741, WO 2006010445, WO 2006016218, US 2006058308, WO 2006033620, WO 2006038871, US 2006084640, US 2006089360, WO 2006058338, WO 2006063178, US 2006128689, WO 2006062981, WO 2006065646, WO 2006068618, WO 2006068592, WO 2006068593, WO 2006076646, US 2006160872, WO 200608082, US 2006183745, WO 2006095263, WO 2006102645, WO 2006100520, US 2006241296, WO 2006122200, WO 2006120481, WO 2006122250, DE 102005044814, WO 2006122772, WO 2006122777, WO 2006124753, WO 2006122799, WO 2006122770, WO 2006122769, WO 2006136245, WO 2007030761, US 20070088072, US 20070088073, US 20070105920, WO 2007042906, WO 2007045462, WO 2007050732; anticonvulsants, such as, carbemazepine, oxcarbemazepine, lamotrigine, gabapentin and pregabalin; NSAIDS, such as, aspirin, acetometaphen, ibuprofen, diclofenac, naproxen, flurbiprofen, indomethacin, piroxicam, ketoprofen, sulindac and diflunisal; COX-2 inhibitors, such as, celecoxib, rofecoxib, lumiracoxib, valdecoxib, etoricoxib and compounds described in WO 2004048314; GABAb receptor modulators, such as, racemic and (R)-baclofen, AZD3355, XP19986 and compounds described in WO 2006001750 and WO 2004000856; CB receptor ligands, such as, dronabinol, nabilone, cannabidiol, rimonabant and compounds described in WO 2002042248 and WO 2003066603; calcium channel blockers, such as, ziconotide, AGI0-003, PD-217014 and compounds described in WO 2006038594, WO 2006030211 and WO 2005068448; sodium channel blockers, such as, lamotrigine and compounds described in WO 2006023757, WO 2005097136, JP 2005206590 and WO 2005047270; tricyclic antidepressants, such as, clomipramine, amoxapine, nortripyline, amitriptyline, imipramine, desipramine, doxepin, trimipramine and protripyline; serotonin and noradrenaline re-uptake inhibitors, such as, milnacipran, desvenlafaxine, sibutramine, duloxetine, fluoxetine, paroxetine, citalopram, sertraline and fluvoxamine; benzodiazepines, such as, levotofisopam, diazepam, lorazepam, clonazepam and alprazolam; alpha-2 receptor agonists, such as, clonidine, tizanidine and guanfacine; ghrelin receptor agonists, such as, ghrelin, ibutamoren, capromorelin, tabimorelin, ipamorelin, 2-Methylalanyl-N-[1(R)-formamido-2-(1H-indol-3-yl)ethyl]-D-tryptophanamide, TZP-101, TZP-102, LY-444711, EX-1314 and compounds described in US 6525203, US 20050154043, WO 2005097788, WO 2006036932, WO 2006135860, US 20060079562, WO 2006010629, WO 2006009674, WO 2006009645, US 20070021331, WO 2007020013, US 20070037857, WO 2007014258, WO 2007113202, WO 2007118852, US 20080194672, US 20080051383 and US 20080051383; corticosteroids, such as, hydrocortisone, cortisone, dexamethasone, betamethasone, beclomethasone, prednisolone, 6-methylprednisolone, budesonide, mometasone furoate, ciclesonide, fluticasone propionate and fluticasone furoate; aminosalicylates, such as, mesalazine, ipsalazide, olsalazine and balsalazide; immunomodulators, such as, azathioprine, 6-mercaptopurine, methotrexate, mycophenolate mofetil, ciclosporin and tacrolimus; PDE4 inhibitors, such as, tetomilast, cilomilast, roflumilast and arofylline; antibiotics, such as, metronidazole, ornidazole and ciprofloxacin; anti-adhesion molecule agents, such as, natalizumab and MLN02; anti IL-2 agents, such as, daclizumab and basilixumab; anti CD-3 agents, such as, visilizumab; and anti-TNF agents, such as, infliximab, adalimumab, fontolizumab and certolizumab pegol; psychiatric medications comprising compounds selected from the group consisting of agomelatine, azapirones, alprazolam, amitriptyline, aniracetam, acetyl-L-carnitine, aripiprazol, acetophenazine, benzodiazepines, barbiturate, buspirone, bupropione, chlordiazepoxide, chlorazepate, clonazepam, chlorpromazine, clozapine, CX614, CX516, chlorprothixene, diphenhydramine hydroxyzine, demoxepam, diazepam, droperidol, duloxetine, donezepil, doxepine, desipramine, flurazepam, fluphenazine, fluoxetine, flupentixol, gabapentin, melatonin, ginkgo-derived compounds, galantamine, haloperidol, Hydergine (ergoloid mesylates), huperzine, isocarboxazid, imipramine, lorazepam, loxapine, meprobamate, medazepam, moclobemide, molindone, maprotiline, modafinil, memantine, methylphenicate, mesoridazine, methotrimeprazine, nortriptyline, naproxen, oxazepam, oxiracetam, olanzapine, prazepam, paroxetine, phenelzine, pipotiazine, perphenazine, promazine, pimozide, PDE4 inhibitors, quazepam, quetiapine, reboxetine, rivastigmine, prochlorperazine, risperidone, sertraline, sertindole, temazepam, triazolam, tranylcypromine, tomoxetine, thiotixene, trifluoperazine, thioridazine, zolpidem and ziprasidone.

A preferred group of compounds which may be mentioned are compounds of formula II;

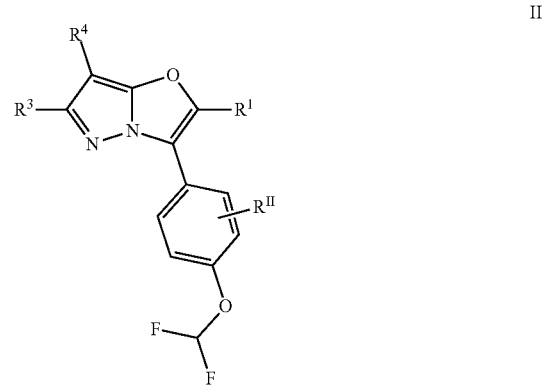

in which $R^1$, $R^3$ and $R^4$ are each as hereinbefore defined; and $R^{II}$ is alkyl C1 to 6, alkoxy C1 to 6, halo, haloalkyl C1 to 6, thioalkyl C1 to 6, —$NR^5R^6$, —CN, haloalkoxy C1 to 6, aryl or —Het or two adjacent carbons are substituted by —$O(CH_2)_xO(CH_2)_y$—;

Het is a 5- or 6-membered heteroaryl or a 4, 5- or 6-membered heterocycle; and $R^5$, $R^6$, x and y are each as hereinbefore defined;

and isomers thereof,
in free form or as a pharmaceutically acceptable salt.

An alternative preferred group of compounds which may be mentioned are compounds of formula III;

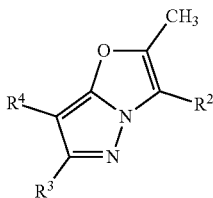

in which $R^2$, $R^3$ and $R^4$ are each as hereinbefore defined;
and isomers thereof,
in free form or as a pharmaceutically acceptable salt.

An alternative preferred group of compounds are compounds of formula IV;

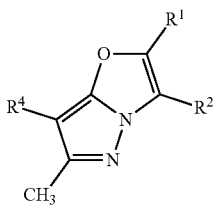

in which $R^1$, $R^2$ and $R^4$ are each as hereinbefore defined;
in free form or as a pharmaceutically acceptable salt.

An alternative preferred group of compounds are compounds of formula V;

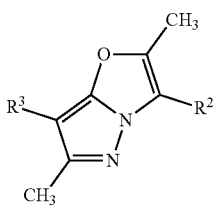

in which $R^2$ and $R^4$ are each as hereinbefore defined;
and isomers thereof; in free form or as a pharmaceutically acceptable salt.

An alternative preferred group of compounds are compounds of formula I;

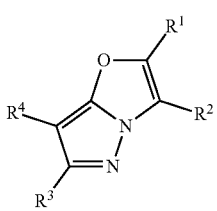

in which $R^4$ is a 5- or 6-membered heteroaryl being optionally substituted by one or more substituents selected from the group alkyl C1 to 10, haloalkyl C1 to 10, hydroxyalkyl C1 to 10, alkoxy(C1 to 3)alkyl(C1 to 3), —$CO_2R^{19}$, —$CONR^{20}R^{21}$, or a 5- or 6-membered heterocycle or heteroaryl; and $R^1$, $R^2$, $R^3$, $R^{19}$, $R^{20}$ and $R^{21}$ are each as hereinbefore defined;
and isomers thereof;
in free form or as a pharmaceutically acceptable salt.

According to this aspect of the invention a preferred group of compounds are compounds of formula VI;

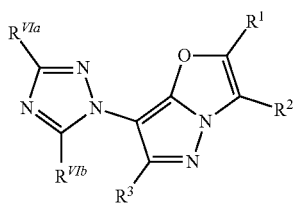

in which R1, $R^2$ and R3 are each as hereinbefore defined; and $R^{VIa}$ and $R^{VIb}$, which may be the same or different, are each hydrogen or alkyl C1 to 6;
and isomers thereof;
in free form or as a pharmaceutically acceptable salt.

Acid addition salts may be produced from the free bases in known manner, and vice-versa.

Compounds of the present invention are either obtained in the free form, as a salt thereof, or as prodrug derivatives thereof.

As used herein, the term "pharmaceutically acceptable salt" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids, e.g., acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Inorganic acids from which salts can be derived include, for example, hydrochloric acid, hydrobromic acid, sulphuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulphonic acid, ethanesulphonic acid, p-toluenesulphonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminium, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

A prodrug is a compound which is converted to a therapeutically active compound after administration. For example, conversion may occur by hydrolysis of an ester group or some other biologically labile group. Prodrug preparation is well known in the art. For example "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral centre of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centres and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Compounds of formula (I) in optically pure form, where appropriate, can be obtained from the corresponding racemates according to well-known procedures, e.g., HPLC with chiral matrix. Alternatively, optically pure starting materials can be used.

Stereoisomeric mixtures, e.g., mixtures of diastereomers, can be separated into their corresponding isomers in a manner known per se by means of suitable separation methods. Diastereomeric mixtures, e.g., may be separated into their individual diastereomers by means of fractionated crystallisation, chromatography, solvent distribution and similar procedures. This separation may take place either at the level of a starting compound or in a compound of formula (I) itself. Enantiomers may be separated through the formation of diastereomeric salts, e.g., by salt formation with an enantiomer-pure chiral acid, or by means of chromatography, e.g., by HPLC, using chromatographic substrates with chiral ligands.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral centre of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centres and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

According to a further aspect of the invention we provide a method of treatment or alleviation of any state with increased endogenous level of CRF or in which the HPA (hypothalamic pituitary axis) is disregulated, or of various diseases induced or facilitated by CRF which comprises administering to a mammal a therapeutically effective amount of a compound of formula I, or a salt thereof, as hereinbefore described.

We further provide a pharmaceutical composition comprising a compound of formula I as hereinbefore described, in free form or in pharmaceutically acceptable salt form, in association with a pharmaceutically acceptable adjuvant, diluent or carrier.

The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers etc.

Typically, the pharmaceutical compositions are tablets and gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminium silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavours and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavouring agents, colouring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilisers, stabilizers, tonicity enhancing agents, buffers and preservatives.

As used herein a topical application may also pertain to an inhalation or to an intranasal application. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavouring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by CRF, or (ii) associated with CRF activity, or (iii) characterized by abnormal activity of CRF; or (2) reducing or inhibiting the activity of CRF; or (3) reducing or inhibiting the expression of CRF. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of CRF; or at least partially reducing or inhibiting the expression of CRF. The meaning of the term "a therapeutically effective amount" as illustrated in the above embodiment for CRF also applies by the same means to any other relevant proteins/peptides/enzymes.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Compounds of the present invention are either obtained in the free form, as a salt thereof, or as prodrug derivatives thereof When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the α-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

The present invention includes all pharmaceutically acceptable isotopically-labeled compounds of the invention, i.e. compounds of formula (I), wherein (1) one or more atoms are replaced by atoms having the same atomic number, but an atomic mass or mass number different from the atomic mass or mass number usually found in nature, and/or (2) the isotopic ratio of one or more atoms is different from the naturally occurring ratio.

Examples of isotopes suitable for inclusion in the compounds of the invention comprises isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labeled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula I that contain groups capable of acting as donors and/or acceptors for hydrogen bonds may be capable of forming co-crystals with suitable co-crystal formers. These co-crystals may be prepared from compounds of formula I by known co-crystal forming procedures. Such procedures include grinding, heating, co-subliming, co-melting, or contacting in solution compounds of formula I with the co-crystal former under crystallization conditions and isolating co-crystals thereby formed. Suitable co-crystal formers include those described in WO 2004/078163. Hence the invention further provides co-crystals comprising a compound of formula I.

The pharmaceutical compositions for separate administration of the combination partners and for the administration in a fixed combination, i.e., a single galenical composition comprising at least two combination partners, according to the invention can be prepared in a manner known per se and are those suitable for enteral, such as oral or rectal, and parenteral administration to mammals, including man, comprising a therapeutically effective amount of at least one pharmacologically active combination partner alone or in combination with one or more pharmaceutically acceptable carriers, especially suitable for enteral or parenteral application.

Pharmaceutical compositions contain, e.g., from about 0.1% to about 99.9%, preferably from about 20% to about 60%, of the active ingredients. Pharmaceutical preparations for the combination therapy for enteral or parenteral administration are, e.g., those in unit dosage form, such as tablets including sugar-coated tablets, capsules, suppositories and ampoules. These are prepared in a manner known, per se, e.g., by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

According to an additional aspect of the invention we provide a process for the manufacture of a compound of formula I as hereinbefore described which comprises one or more of the following steps;

A:
(i) the condensation of a compound of formula VIa;

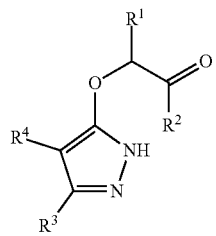

VIa in which $R^1$, $R^2$, $R^3$ and $R^4$ are each as hereinbefore defined;
(ii) reacting a compound of formula VII;

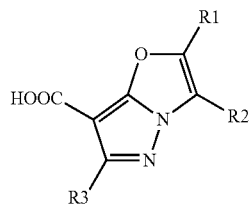

VII in which $R^1$, $R^2$ and $R^3$ are each as hereinbefore defined; with a compound of formula VIII

NHR$^{13}$R$^{14}$     VIII in which $R^{13}$ and $R^{14}$ are each as hereinbefore defined;
(iii) reacting a compound of formula IX;

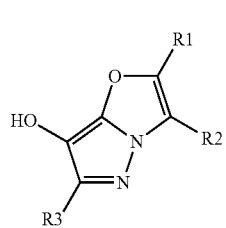

IX in which $R^1$, $R^2$ and $R^3$ are each as hereinbefore defined; with a compound of formula X

R$^7$OH     X in which $R^7$ is as hereinbefore defined;
(iv) reducing a compound of formula XI;

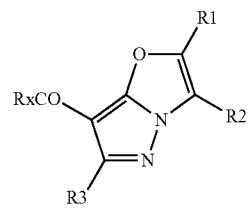

XI in which $R^1$, $R^2$ and $R^3$ are each as hereinbefore defined; and $R^x$ is alkyl C1 to 5;
(v) reacting a compound of formula XII;

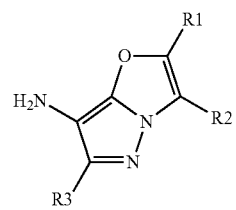

XII in which $R^1$, $R^2$ and $R^3$ are each as hereinbefore defined; with a compound of formula XIII or XIV;

R$^{12}$CHO     XIII

R$^{17}$COR$^{18}$     XIV in which $R^{12}$ is as hereinbefore defined; and
$R^{17}$ and $R^{18}$, which may be the same or different, are each alkyl C1 to 6; or
(vi) reacting a compound of formula XV;

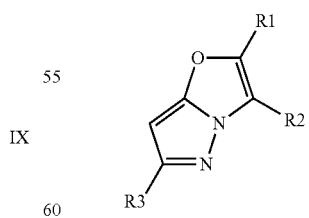

XV in which $R^1$, $R^2$ and $R^3$ are each as hereinbefore defined; with a compound of formula XVI;

R$^8$R$^9$NH     XVI in which R⁸ and R⁹ are as hereinbefore defined; and
B: reacting a compound of formula IV;

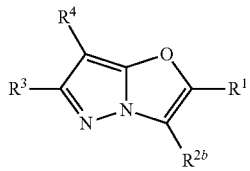

in which R¹, R³ and R⁴ are each as hereinbefore defined; and
R²ᵇ is a phenolic group, which may be optionally substituted as hereinbefore described;
with a 2-chloro-2,2-difluoroacetate.

In any additional process steps, carried out as desired, functional groups of the starting compounds which should not take part in the reaction may be present in unprotected form or may be protected e.g., by one or more of the protecting groups mentioned below. The protecting groups are then wholly- or partly-removed according to one of the methods described there.

The protecting groups may already be present in precursors and should protect the functional groups concerned against unwanted secondary reactions. It is a characteristic of protecting groups that they lend themselves readily, i.e., without undesired secondary reactions, to removal, typically by solvolysis, reduction, photolysis or also by enzyme activity, e.g., under conditions analogous to physiological conditions, and that they are not present in the end-products. The skilled artisan knows, or can easily establish, which protecting groups are suitable with the reactions mentioned hereinabove and hereinafter.

The protection of such functional groups by protecting groups, the protecting groups themselves, and their removal reactions are described, e.g., in standard reference works, such as J. F. W. McOmie, *Protective Groups in Organic Chemistry*, Plenum Press, London and NY (1973); T. W. Greene, *Protective Groups in Organic Synthesis*, Wiley, NY (1981); The Peptides; Volume 3, E. Gross and J Meienhofer, Eds., Academic Press, London and NY (1981); *Methoden der organischen Chemie (Methods of organic chemistry)*, Houben Weyl, 4ᵗʰ Edition, Volume 15/1, Georg Thieme Verlag, Stuttgart (1974); H. D. Jakubke and H. Jescheit, *Aminosauren, Peptide, Proteine (Amino acids, peptides, proteins)*, Verlag Chemie, Weinheim, Deerfield Beach, and Basel (1982); and Jochen Lehmann, *Chemie der Kohlenhydrate: Monosaccharide and Derivate (Chemistry of carbohydrates monosaccharides and derivates)* Georg Thieme Verlag., Stuttgart (1974).

All process steps described herein can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, e.g., ion exchangers, typically cation exchangers, e.g., in the H⁺ form, depending on the type of reaction and/or reactants at reduced, normal or elevated temperature, e.g., in the range from −100° C. to about 190° C., preferably from about −80° C. to about 150° C., e.g., at −80° C. to 60° C., at room temperature, at −20° C. to 40° C. or at the boiling point of the solvent used, under atmospheric pressure or in a closed vessel, where appropriate under pressure, and/or in an inert atmosphere, e.g., under argon or nitrogen.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Intermediates useful in the preparation of the compounds of the invention are described in co-pending International patent application No. PCT/EP2009/060094.

Compounds of formula I may be prepared by the general reactions (it should be noted that the group R referred to in the reaction sequences below are for illustrative purposes only and do not precisely correspond to the R groups hereinbefore defined).

Referring to the examples that follow, compounds of the preferred embodiments are synthesized using the methods described herein, or other methods, which are known in the art.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

It is understood that the invention is not limited to the embodiments set forth herein for illustration, but embraces all such forms thereof as come within the scope of the above disclosure.

Experimental Details:
General Methods
¹H-NMR: Run on either Bruker Ultrashield™ 400 (400 MHz) spectrometer or are run on open access Bruker AVANCE 400 NMR spectrometers using ICON-NMR. Spectra are measured at 298K and are referenced using the solvent peak, chemical shifts (δ-values) are reported in ppm, coupling constants (J) are given in Hz, spectra splitting pattern are designated as singlet (s), doublet (d), triplet (t), quadruplet (q), multiplet or more overlapping signals (m), broad signal (br), solvent is given in parentheses.

MS: These are either Agilent 1100 HPLC/Micromass Platform Mass Spectrometer combinations or Waters Acquity UPLC with SQD Mass Spectrometer or Waters Alliance HT HPLC system equipped with a MS detector Waters MicromassZQ or Waters Micromass Platform LCZ system. Mass spectra are run on LCMS systems using electrospray ionization. [M+H]+ refers to mono-isotopic molecular weights.

HPLC: Waters Alliance HPLC system, retention times for system A (⁴t$_{Ret}$) are reported in min, linear gradient 5-100% CH₃CN and H₂O (0.1% TFA) in 4 min+0.5 min 100% CH₃CN, PDA MaxPlot detection (210.0 nm to 400.0 nm), flow rate 3 ml/min at 35° C., the column is a Sunfire™ C18, 4.6×20 mm, 3.5 μm.

prep-HPLC: Waters HPLC prep-system, UV detector Waters 2487 Dual λ Absorbance Detector or MS detector Waters micromassZQ, reversed phase column SunFire™ Prep, C18 OBD, 100×30 mm, 5 μm, or 100×19 mm, 5 μm, gradient elution (CH₃CN/water with 0.1% TFA), generally product obtained as a TFA salt after lyophilisation.

TLC: Precoated silica gel 60 F₂₅₄ glass plates (Merck), visualization by UV light (254 nm).

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

General Conditions:

1H-NMR: Spectra are run on either a Bruker Ultrashield™ 400 (400 MHz) spectrometer or on a Bruker AVANCE 400 NMR spectrometer using ICON-NMR. Spectra are measured at 298K and are referenced using the solvent peak, chemical shifts (δ-values) are reported in ppm, coupling constants (J) are given in Hz, spectra splitting pattern are designated as singlet (s), doublet (d), triplet (t), quadruplet (q), multiplet or more overlapping signals (m), broad signal (br), solvent is given in parentheses.

MS: These are either Agilent 1100 HPLC/Micromass Platform Mass Spectrometer combinations or Waters Acquity UPLC with SQD Mass Spectrometer or Waters Alliance HT HPLC system equipped with a MS detector Waters MicromassZQ or Waters Micromass Platform LCZ system. Mass spectra are run on LCMS systems using electrospray ionization. [M+H]+ refers to mono-isotopic molecular weights.

The various starting materials, intermediates, and compounds of the preferred embodiments may be isolated and purified, where appropriate, using conventional techniques such as precipitation, filtration, crystallization, evaporation, distillation, catch and release, and chromatography. Unless otherwise stated, all starting materials are obtained from commercial suppliers and used without further purification. Salts may be prepared from compounds by known salt-forming procedures.

In addition various trade reagents and materials available from have been utilized. Such reagents and materials include IST PE-AX/SCX-2 and SCX-2 cartridges and can be readily obtained from the suppliers indicated.

For the examples below as well as throughout the application, the following abbreviations have the following meanings If not defined, the terms have their generally accepted meanings.

Abbreviations:
DCM dichloromethane
DMF N,N-dimethylformamide
DMSO dimethylsulfoxide
eq. equivalent
EtOAc ethyl acetate
EtOH ethanol
h hour
HPLC high performance liquid chromatography
HPLC high pressure liquid chromatography
LCMS liquid chromatographic mass spectroscopy
MeOH methanol
min minute
MS mass spectroscopy
NBS N-bromosuccinimide
NMR nuclear magnetic resonance
O/N overnight
prep-HPLC preparative high pressure liquid chromatography
Rt Retention time
RT room temperature
TFA trifluoroacetic acid
THF tetrahydrofuran If not indicated otherwise, the analytical HPLC conditions are as follows:

Method 10minLC_v001

| Column | Waters BEH C18 100 × 2.1 mm, 1.7 μm |
| --- | --- |
| Column Temperature | 50° C. |
| Eluents | A: H2O, B: acetonitrile, both containing 0.1% TFA |
| Flow Rate | 0.7 mL/min |
| Gradient | 0.25 min 5% B; 5% to 95% B in 7.75 min, 1.00 min 95% B |

Method 10minLC_v002

| Column | Waters BEH C18 50 × 2.1 mm, 1.7 μm |
| --- | --- |
| Column Temperature | 50° C. |
| Eluents | A: H2O, B: methanol, both containing 0.1% TFA |
| Flow Rate | 0.8 mL/min |
| Gradient | 0.20 min 5% B; 5% to 95% B in 7.80 min, 1.00 min 95% B |

Method 2minLC 30 v002

| Column | Waters BEH C18 50 × 2.1 mm, 1.7 μm |
| --- | --- |
| Column Temperature | 50° C. |
| Eluents | A: H2O, B: methanol, both containing 0.1% TFA |
| Flow Rate | 0.8 mL/min |
| Gradient | 0.25 min 30% B; 30% to 95% B in 1.00 min, 0.25 min 95% B |

Method LowpH_v001

| Column | Phenomenex Gemini C18 50 × 4.6 mm, 3.0 μm |
| --- | --- |
| Column Temperature | 40° C. |
| Eluents | A: H2O, B: acetonitrile, both containing 0.1% TFA |
| Flow Rate | 1.0 mL/min |
| Gradient | 5% to 95% B in 2.0 min, 0.2 min 95% B |

PREPARATION OF EXAMPLE

Example 1

3-(4-(Difluoromethoxy)-2-methylphenyl)-7-(3,5-dimethyl-1H-1,2,4-triazol-1-yl)-2,6-dimethylpyrazolo[5,1-b]oxazole

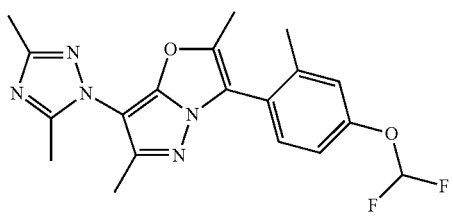

Step 1: 4-(7-(3,5-Dimethyl-1H-1,2,4-triazol-1-yl)-2,6-dimethylpyrazolo[5,1-b]oxazol-3-yl)-3-methylphenol 7-(3,5-Dimethyl-[1,2,4]triazol-1-yl)-3-(4-methoxy-2-methyl-phenyl)-2,6-dimethyl-pyrazolo[5,1-b]oxazole (Intermediate C) (100 mg, 0.285 mmol) was dissolved in dry DCM (5 ml). The mixture was placed under an atmosphere of flushed with $N_2$ and treated with boron tribromide (1.423 ml, 1.423 mmol) dropwise at RT. After approximately 30 mins, the reaction was quenched by careful addition of $H_2O$. The mixture was transferred to a separating funnel and extracted with DCM (50 ml). The organic portion was separated and washed with 1M HCl, 1M NaOH, brine, dried ($MgSO_4$) and evaporated in vacuo to give a brown solid. Trituration with EtOAc afforded the title compound as an off white solid. LC-MS Rt 1.02 mins; MS m/z 338.2 [M+H]+; Method=2minLC_30_v002. $^1$H NMR (400 MHz, DMSO-d6) δ 7.25 (d, 1H), 6.8 (s, 1H), 6.75 (d, 1H), 2.35 (s, 3H), 2.30 (s, 6H), 2.2 (s, 3H), 2.15 (s, 3H).

Step 2: 3-(4-(Difluoromethoxy)-2-methylphenyl)-7-(3,5-dimethyl-1H-1,2,4-triazol-1-yl)-2,6-dimethylpyrazolo[5,1-b]oxazole A solution of 4-(7-(3,5-dimethyl-1H-1,2,4-triazol-1-yl)-2,6-dimethylpyrazolo[5,1-b]oxazol-3-yl)-3-methylphenol (Step 1) (100 mg, 0.296 mmol) in dry DMF (4 ml) was treated with potassium carbonate (205 mg, 1.482 mmol) and stirred under N2 for 30 mins at 50° C. Methyl 2-chloro-2,2-difluoroacetate (428 mg, 2.96 mmol) was added and the reaction was heated to 90° C. for 1.5 hrs. After cooling to RT, the mixture was partitioned between EtOAc and water. The organic portion was washed with brine, dried (MgSO4) and concentrated in vacuo to give a brown oil. Purification of the crude product by reverse phase chromatography [prep-HPLC (Waters system)] yielded the title compound (TFA salt) as a colourless oil. The salt was taken up in DCM (2 ml) and MP-carbonate resin (macroporous polystyrene anion-exchange resin) (500 mg, 2.8 mmol/g, Argonaut) was added and the contents stirred at RT for 30 mins. The resin was filtered, washed with DCM and the filtrate was concentrated in vacuo to give the title compound as the free base. LC-MS Rt 4.86 mins; MS m/z 388.2 [M+H]+; Method=10minLC_v002. 1H NMR (400 MHz, CDCl3) δ 7.4 (1H, d), 7.15 (1H, s), 7.10 (1H, d), 6.6 (1H, t), 2.40 (6H, m), 2.35 (6H, m), 2.20 (3H, s).

Preparation of Intermediates

Intermediate A 4-(3,5-Dimethyl-[1,2,4]triazol-1-yl)-5-methyl-2H-pyrazol-3-ol

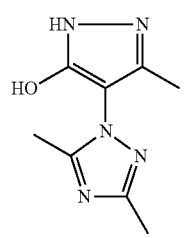

Step 1: 2-Bromo-3-oxo-butyric acid benzyl ester

To a stirring dispersion of benzyl acetoacetate (20 ml, 116 mmol) and NBS (21.64 g, 122 mmol) in $Et_2O$ (1000 ml) was added ammonium acetate (0.893 g, 11.58 mmol). The reaction was stirred at RT for 4 hours and then filtered, washed with water (400 ml), brine, dried over $MgSO_4$ and concentrated in vacuo to give the title compound as a yellow oil; 1H NMR (400 MHz, $CDCl_3$) δ 7.37-7.42 (5H, m, 5×ArH), 5.27 (2H, s, ArCH2OR), 4.82 (1H, s, CHBr), 2.42 (3H, s, RCOCH3).

Step 2: Benzyl 2-(3,5-dimethyl-1H-1,2,4-triazol-1-yl)-3-oxobutanoate

To a stirring solution of 3,5-dimethyl-1-H-[1,2,4]-triazole (0.502 g, 5.16 mmol) in THF (36.9 ml) was added NaH (0.199 g, 4.98 mmol). After stirring at RT for 10 mins 2-bromo-3-oxo-butyric acid benzyl ester (step 1) (1.0 g, 3.69 mmol) was added. The mixture was stirred at 40° C. for 30 mins and then allowed to cool to RT. The mixture was absorbed onto silica and purification by chromatography on silica eluting with 0-10% DCM/MeOH afforded the title compound as an orange oil; LC-MS Rt 1.95 mins; MS m/z 288.3 [M+H]+; Method LowpH_v001.

Step 3: 4-(3,5-Dimethyl-[1,2,4]triazol-1-yl)-5-methyl-2H-pyrazol-3-ol

A mixture comprising benzyl 2-(3,5-dimethyl-1H-1,2,4-triazol-1-yl)-3-oxobutanoate (step 2) (7.1 g, 24.71 mmol) and hydrazine (2.327 ml, 74.1 mmol) in EtOH (124 ml) were stirred at 50° C. for 3 hours. The reaction was allowed to cool to RT overnight. The resultant solid was then collected by filtration and washed with a small amount of cold EtOH to afford the title compound as a pale yellow solid; LC-MS Rt 0.61 mins; MS m/z 193.9 [M+H]+; Method=Method LowpH_v001.

Intermediate B

2-Bromo-1-(4-methoxy-2-methyl-phenyl)-propan-1-one

To a stirring dispersion of $CuBr_2$ (11.91 g, 53.3 mmol) in EtOAc (40.0 ml) and chloroform (40 ml) at 60° C. was added 1-(4-methoxy-2-methylphenyl)propan-1-one (4.753 g, 26.7 mmol) and the mixture left to stir for 3.5 hours. The reaction was allowed to cool to RT and filtered through Celite®, washing the filter cake with EtOAc. The filtrate was reduced in vacuo to yield a dark brown oil. Purification of the oil by chromatography on silica eluting with 10% EtOAc/iso-hexane afforded the title compound as a pale yellow oil; $^1$H NMR (400 MHz, CDCl3) δ7.77 (d, 1H), 6.80 (m, 2H), 5.25 (q, 1H), 3.89 (s, 3H), 2.58 (s, 3H), 1.90 (d, 3H).

Intermediate C 7-(3,5-Dimethyl-[1,2,4]triazol-1-yl)-3-(4-methoxy-2-methyl-phenyl)-2,6-dimethyl-pyrazolo[5,1-b]oxazole Step 1: 2-[4-(3,5-Dimethyl-[1,2,4]triazol-1-yl)-5-methyl-2H-pyrazol-3-yloxy]-1-(4-methoxy-2-methyl-phenyl)-propan-1-one To a stirring solution of 4-(3,5-dimethyl-[1,2,4]triazol-1-yl)-5-methyl-2H-pyrazol-3-ol (1 g, 5.18 mmol) (Intermediate A) in DMF (25 ml) was added Cs$_2$CO$_3$ (1.771 g, 5.43 mmol). The mixture was left to stir at 50° C. for 30 minutes and then treated with of 2-bromo-1-(4-methoxy-2-methyl-phenyl)-propan-1-one (Intermediate B) (1.397 g, 5.43 mmol) in DMF (10 ml). The mixture was stirred at 50° C. for 1 hour and concentrated in vacuo. The residue was dissolved in water (300 ml) and extracted with EtOAc (3×150 ml). The combined organic extracts were washed with NaHCO$_3$, water, dried (MgSO$_4$) and concentrated in vacuo to yield a pale yellow solid. Purification of the solid by chromatography on silica eluting with 20-100% EtOAc in iso-hexane afforded the title compound as a white solid; LC-MS Rt 1.03 mins; MS m/z 370.3 [M+H]+; Method 2minLC_30_v002.

Step 2: 7-(3,5-Dimethyl-[1,2,4]triazol-1-yl)-3-(4-methoxy-2-methyl-phenyl)-2,6-dimethyl-pyrazolo[5,1-b]oxazole To a dispersion of 2-[4-(3,5-dimethyl-[1,2,4]triazol-1-yl)-5-methyl-2H-pyrazol-3-yloxy]-1-(4-methoxy-2-methyl-phenyl)-propan-1-one (step 1) (0.905 g, 2.45 mmol) in 1,2-dichloroethane (20 ml) was added titanium tetrachloride (0.675 ml, 6.12 mmol). The reaction mixture was heated to 85° C. for 2.5 hours and left at RT overnight. The mixture was quenched carefully with sat. NH$_4$Cl (50 ml) and extracted with EtOAc (2×50 ml). The combined organic extracts were washed with NaHCO$_3$ (50 ml), brine, dried (MgSO$_4$) and concentrated in vacuo to afford a dark brown oil. The crude oil was then taken up in 10% Et$_2$O/iso-hexane (50 ml) and the brown solution was sonicated. The resulting solid was collected and washed with iso-hexane to give a cream coloured solid. Purification of this solid by recrystallisation from hot Et$_2$O (~40 ml) yielded the title compound as tan crystals; LC-MS Rt 3.7 mins; MS m/z 352.1 [M+H]+; Method=10minLC_v001.

$^1$H NMR (400 MHz, DMSO-d$_6$) δ 7.39 (1H, d), 7.01 (1H, d), 6.94 (1H, dd), 3.83 (3H, s), 2.30 (6H, s), 2.26 (6H, s), 2.11 (3H, s).

Biological Data

The compound of Example 1 is 0.071 μm (hCRF1ANTAG/IC50 [μmol 1-1]).

The invention claimed is:
1. A compound of formula I;

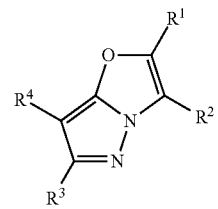

in which R$^1$ and R$^3$, which may be the same or different, are each hydrogen, alkyl C1 to 6 or halo alkyl C1 to 6;

R$^2$ is difluoromethoxyphenyl, in which the phenyl may be optionally substituted by one or more of alkyl C1 to 6, alkoxy C1 to 6, halo, haloalkyl C1 to 6, thioalkyl C1 to 6, —NR$^5$R$^6$, —CN, haloalkoxy C1 to 6, aryl or -Het or two adjacent carbons are substituted by —O(CH$_2$)$_x$O (CH$_2$)$_y$—;

Het is a 5- or 6-membered heteroaryl or a 4, 5- or 6-membered heterocycle;

R$^4$ is alkylene C2 to 10, hydroxy alkyl C1 to 10, each of which may optionally be substituted by aryl, or is —OR$^7$, —(CH$_2$)$_m$NR$^8$R$^9$, —COR$^{10}$, a 5- or 6-membered heteroaryl or a 5- or 6-membered heterocycle, the 5- or 6-membered heteroaryl or 5- or 6-membered heterocycle being optionally substituted by one or more substituents selected from the group alkyl C1 to 10, haloalkyl C1 to 10, hydroxyalkyl C1 to 10, alkoxy(C1 to 3)alkyl(C1 to 3), halo, —CO$_2$R$^{19}$, —CONR$^{20}$R$^{21}$, aryl or a 5- or 6-membered heterocycle or heteroaryl;

R$^5$ and R$^6$, which may be the same or different, are each hydrogen or alkyl C1 to 6 or R$^5$ and R$^6$, together with the nitrogen to which they are attached, form an optionally substituted saturated or unsaturated cyclic group;

R$^7$ is alkyl C1 to 10, cycloalkyl C3 to 10, optionally fused to an aryl, alkyl(C1 to 6)-cycloalkyl(C3 to 6)-, hydroxy alkyl C1 to 10, hydroxyalkyl(C1 to 6)-(haloalkyl C1 to 6), alkyl(C1 to 6)-oxy-alkyl(C1 to 6), —(CH$_2$)$_q$COOR$^{22}$ or a 5- or 6-membered heterocycle; each of which is optionally substituted by one or more of alkyl C1 to 10, alkoxy C1 to 10, hydroxyalkyl C1 to 10, aryl or a 5- or 6-membered heteroaryl, the aryl or a 5- or 6-membered heteroaryl being optionally substituted by alkyl C1 to 10;

R$^8$ and R$^9$, which may be the same or different, are each hydrogen, alkyl C1 to 10, halo alkyl C1 to 10, alkyl(C1 to 6)-oxy-alkyl(C1 to 6), —COOR$^{11}$, —COR$^{12}$ or arylalkyl C1 to 6 or together with the nitrogen to which they are attached R$^8$ and R$^9$ form a 5- or 6-membered heterocycle, optionally substituted by one or more of alkyl C1 to 6;

m is an integer 0 or 1;
q is an integer from 1 to 6;
x and y, which may be the same or different, are each an integer from 1 to 6;
R$^{10}$ is hydrogen, alkyl C1 to 6, —NR$^{13}$R$^{14}$, hydroxy or alkoxy C1 to 6;
R$^{12}$ is alkyl C1 to 10, aryl or is a 5- or 6-membered unsaturated heterocyclic ring;
R$^{13}$ and R$^{14}$, which may be the same or different, are each alkyl C1 to 10, cycloalkyl C3 to 10, cycloalkyl(C3 to 6)alkyl(C1 to 6)-, alkoxy C1 to 10, haloalkyl C1 to 10, aryl, a 5- or 6-membered heterocycle or heteroaryl comprising 1, 2 or 3 heteroatoms; each of which may be optionally substituted by aryl or heteroaryl, or R$^{13}$ and R$^{14}$ together with the nitrogen to which they are attached form a 5- or 6-membered heterocycle comprising 1, 2 or 3 heteroatoms, which may optionally be fused to a phenyl group, said heterocycle and optionally fused phenyl group being optionally substituted by one or more of alkoxy C1 to 10;

$R^{22}$ is hydrogen or alkyl C1 to 6;

$R^{11}$ is alkyl C1 to 6 or aryl;

$R^{19}$ is hydrogen or alkyl C1 to 10;

$R^{20}$ and $R^{21}$, which may be the same or different, are each alkyl C1 to 10;

in free form or as a pharmaceutically acceptable salt.

2. A compound according to claim 1 wherein the compound is of formula II;

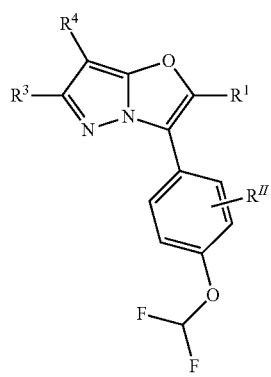

II in which $R^1$, $R^3$ and $R^4$ are each as defined in claim 1; and $R^{II}$ is alkyl C1 to 6, alkoxy C1 to 6, halo, haloalkyl C1 to 6, thioalkyl C1 to 6, —$NR^5R^6$, —CN, haloalkoxy C1 to 6, aryl or -Het or two adjacent carbons are substituted by —$O(CH_2)_xO(CH_2)_y$—;

Het is a 5- or 6-membered heteroaryl or a 4, 5- or 6-membered heterocycle; and $R^5$, $R^6$, x and y are each as defined in claim 1;

in free form or as a pharmaceutically acceptable salt.

3. A compound according to claim 1 wherein the compound is of formula III;

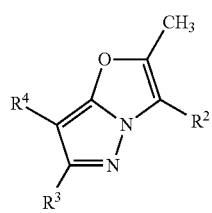

III in which $R^2$, $R^3$ and $R^4$ are each as defined in claim 1;

in free form or as a pharmaceutically acceptable salt.

4. A compound according to claim 1 wherein the compound is of formula IV;

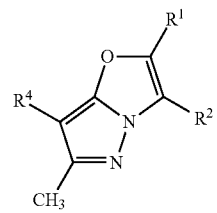

IV in which $R^1$, $R^2$ and $R^4$ are each as defined in claim 1;

in free form or as a pharmaceutically acceptable salt.

5. A compound according to claim 1 wherein the compound is of formula V;

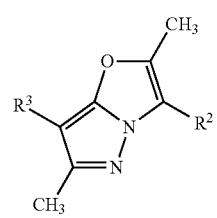

V in which $R^2$ and $R^4$ are each as defined in claim 1;

in free form or as a pharmaceutically acceptable salt.

6. A compound according to claim 1 wherein the compound is of formula I;

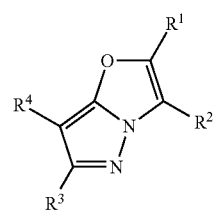

I in which $R^4$ is a 5- or 6-membered heteroaryl being optionally substituted by one or more substituents selected from the group alkyl C1 to 10, haloalkyl C1 to 10, hydroxyalkyl C1 to 10, alkoxy(C1 to 3)alkyl(C1 to 3), —$CO_2R^{19}$, —$CONR^{20}R^{21}$, or a 5- or 6-membered heterocycle or heteroaryl; and $R^1$, $R^2$, $R^3$, $R^{19}$, $R^{20}$ and $R^{21}$ are each as defined in claim 1;

in free form or as a pharmaceutically acceptable salt.

7. A compound according to claim 6 wherein the compound is of formula VI:

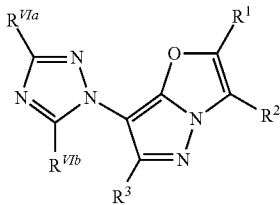

in which R1, R² and R3 are each as defined in claim 6; and R^{VIa} and R^{VIb}, which may be the same or different, are each hydrogen or alkyl C1 to 6;
in free form or as a pharmaceutically acceptable salt.

8. A compound according to claim 1 which is 3-(4-(difluoromethoxy)-2-methylphenyl)-7-(3,5-dimethyl-1H-1,2,4-triazol-1-yl)-2,6-dimethylpyrazolo[5,1-b]oxazole;
in free form or as a pharmaceutically acceptable salt.

9. A method to slow or arrest or reduce the development of irritable bowel syndrome with or without diarrhoea, inflammatory bowel diseases, post-operative ileus, reflux disease and infectious diarrhoea, or at least one of the clinical symptoms thereof, which comprises administering to a subject in need thereof an effective amount of a compound according to claim 1 in free form or as a pharmaceutically acceptable salt.

10. A pharmaceutical composition comprising a compound according to claim 1 in free form or in pharmaceutically acceptable salt form, in association with a pharmaceutically acceptable adjuvant, diluent or carrier.

11. A pharmaceutical composition comprising a compound of formula I according to claim 1 in free form or in pharmaceutically acceptable salt form, in combination with another therapeutically active ingredient, optionally in association with a pharmaceutically acceptable adjuvant, diluent or carrier.

* * * * *